(12) United States Patent
Brubaker

(10) Patent No.: US 7,071,001 B2
(45) Date of Patent: Jul. 4, 2006

(54) SYSTEM AND METHOD FOR IN VITRO BLEEDING TIME TESTING

(75) Inventor: Daniel B. Brubaker, Clovis, CA (US)

(73) Assignee: DNK Associates, Inc., Stateline, NV (US)

( * ) Notice: Subject to any disclaimer, the term of this patent is extended or adjusted under 35 U.S.C. 154(b) by 0 days.

(21) Appl. No.: 10/754,776

(22) Filed: Jan. 8, 2004

(65) Prior Publication Data

US 2004/0143174 A1    Jul. 22, 2004

Related U.S. Application Data

(60) Provisional application No. 60/439,186, filed on Jan. 10, 2003.

(51) Int. Cl.
*G01N 33/86* (2006.01)

(52) U.S. Cl. .............. 436/69; 436/63; 422/73; 422/102; 600/369

(58) Field of Classification Search ............. 436/63, 436/69, 177, 178, 180, 169; 435/2, 13; 422/56–58, 422/73, 100, 101, 102; 600/369, 368; 73/64.41
See application file for complete search history.

(56) References Cited

U.S. PATENT DOCUMENTS

| | | | |
|---|---|---|---|
| 2,674,889 A | 4/1954 | Toof | |
| 2,878,715 A | 3/1959 | Rhees et al. | |
| 3,552,395 A | 1/1971 | Bidwell et al. | |
| 3,618,395 A | 11/1971 | Melliger | |
| 3,661,717 A | 5/1972 | Nelson | |
| 3,749,046 A | 7/1973 | Pin | |
| 3,802,272 A | 4/1974 | Bischoff et al. | |
| 3,809,613 A | 5/1974 | Vieth et al. | |
| 3,814,585 A | 6/1974 | Bailly | |
| 3,865,549 A | 2/1975 | Riley | |
| 3,865,726 A | 2/1975 | Chibata et al. | |
| 3,918,908 A | 11/1975 | Moyer et al. | |
| 4,016,044 A | 4/1977 | Fresnel et al. | |
| 4,062,652 A | 12/1977 | Rolfo-Fontana | |

(Continued)

FOREIGN PATENT DOCUMENTS

GB    2096329    3/1981

OTHER PUBLICATIONS

Internet Brochure from Precision Haemostatics entitled "Platelet-Stat-TM Testing Results", pp. 1-11, date unknown.*

(Continued)

*Primary Examiner*—Maureen M. Wallenhorst
(74) *Attorney, Agent, or Firm*—Wells St. John P.S.

(57) ABSTRACT

The invention includes an in vitro bleeding time device having an opening through a sheet of material across an outlet. At least a portion the sheet of material contains a coating which includes collagen type I, fibrinogen, fibronectin, and von Willebrand factor. The invention includes a blood coagulation analysis system which has a device with an internal chamber for receiving a blood sample through an inlet. A sheet of material spans a flowpath through a single device outlet. A controller regulates pressure and or flow rate within the device. The invention includes a method for analyzing blood coagulation. Blood provided into a device chamber flows out through an opening through a sheet of material which spans the device outlet. A controller is utilized to control pressure and/or flow rate within the device by controlling the flow rate into the device during formation of a clot blockage of the opening.

46 Claims, 11 Drawing Sheets

U.S. PATENT DOCUMENTS

| | | |
|---|---|---|
| 4,099,412 A | 7/1978 | Nehrbass |
| 4,247,298 A | 1/1981 | Rippie |
| 4,335,438 A | 6/1982 | Smolen |
| 4,599,219 A | 7/1986 | Cooper et al. |
| 4,604,894 A | 8/1986 | Kratzer et al. |
| 4,606,420 A | 8/1986 | Silver |
| 4,663,127 A | 5/1987 | Jackson et al. |
| 4,681,858 A | 7/1987 | Chaudhari et al. |
| 4,754,657 A | 7/1988 | Schneider |
| 4,855,821 A | 8/1989 | Swon et al. |
| 4,856,909 A | 8/1989 | Mehta et al. |
| 4,861,725 A | 8/1989 | Liau |
| 4,928,603 A | 5/1990 | Rose et al. |
| 4,953,561 A | 9/1990 | Guirguis |
| 4,962,036 A | 10/1990 | Cermak et al. |
| 4,964,310 A | 10/1990 | Schneider |
| 5,011,662 A | 4/1991 | Noormohammadi et al. |
| 5,039,617 A | 8/1991 | McDonald et al. |
| 5,047,211 A | 9/1991 | Sloane, Jr. et al. |
| 5,057,428 A | 10/1991 | Mizutani et al. |
| 5,089,422 A | 2/1992 | Brubaker |
| 5,127,278 A | 7/1992 | Benz |
| 5,137,031 A | 8/1992 | Guirguis |
| 5,139,031 A | 8/1992 | Guirguis |
| 5,142,920 A | 9/1992 | Bart et al. |
| 5,224,489 A | 7/1993 | Guirguis |
| 5,260,872 A | 11/1993 | Copeland et al. |
| 5,276,383 A | 1/1994 | Leighton et al. |
| 5,316,730 A | 5/1994 | Blake et al. |
| 5,339,830 A | 8/1994 | Blake, III |
| 5,358,690 A | 10/1994 | Guirguis |
| 5,372,945 A | 12/1994 | Alchas et al. |
| 5,432,084 A | 7/1995 | Brubaker |
| 5,451,509 A | 9/1995 | Speck |
| 5,572,997 A | 11/1996 | Kanner et al. |
| 5,601,995 A | 2/1997 | Exner |
| 5,612,187 A | 3/1997 | Brubaker |
| 5,613,491 A | 3/1997 | Kanner et al. |
| 5,662,107 A | 9/1997 | Sakariassen |
| 5,716,796 A | 2/1998 | Bull et al. |
| 5,744,098 A * | 4/1998 | Kratzer et al. ................ 422/73 |
| 5,854,076 A | 12/1998 | Kundu et al. |
| 5,854,423 A | 12/1998 | Venegas |
| 5,888,826 A * | 3/1999 | Ostgaard et al. .............. 436/69 |
| 5,952,184 A | 9/1999 | Shaw et al. |
| 5,958,716 A | 9/1999 | Kundu |
| 6,060,323 A | 5/2000 | Jina |
| 6,114,135 A | 9/2000 | Goldstein |
| 6,338,821 B1 | 1/2002 | Jina |
| 6,391,568 B1 | 5/2002 | Schneider et al. |
| 6,410,337 B1 | 6/2002 | Brady et al. |
| 6,638,274 B1 | 10/2003 | Yamamoto |
| 6,702,987 B1 * | 3/2004 | Kundu et al. ................. 422/58 |

OTHER PUBLICATIONS

Fressinaud et al. "Screening for von Willebrand Disease with a New Analyzer Using High Shear-Stress: A Study of 60 Cases". Blood, vol. 91, No. 4, Feb. 15, 1998, pp. 1325-1331.*

Brubaker, An In Vitro Bleeding Time Test; American Journal of Clinical Pathology, vol. 91, No. 4, Apr. 1989, pp. 422-429.

Kratzer et al., Streamline Pattern and Velocity Components of Flow in a Model of a Branching Coronary Vessel, Microvascular Research, vol. 31, 1986, pp. 250-265.

Burka et al. "A Protocol for Cryoprecipitate Production", Transfusion, vol. 15, No. 4, Jul.-Aug. 1975, p. 307-311.

Nguyen et al., Thrombolysis Using Liposomal Encapsulated Streptokinase: An In Vitro Study, P.S.E.B.M., vol. 192, 1992, pp. 261-269.

Wu et al., Transport Phenomena and Clot Dissolving Therapy: An Experimental Investigation of Diffusion Controlled and Permeation-Enhanced Fibrinolysis, Thrombosis and Haemostasis, 1994, vol. 72, No. 1, pp. 105-112.

Blinc et all, Flow Through Clots Determines the Rate and Pattern of Fibrinolysis, Thrombosis and Heamostasis, 1994, vol. 71, No. 2, pp. 230-235.

Brubaker et al., In Vitro Bleeding Time Test Can Diagnose Thrombotic Thrombocytopenia Purpura and Can Possibly Monitor Therapeutic Plasma Apheresis. Journal of Clinical Apheresis, Jan. 2000, pp. 1-8.

* cited by examiner

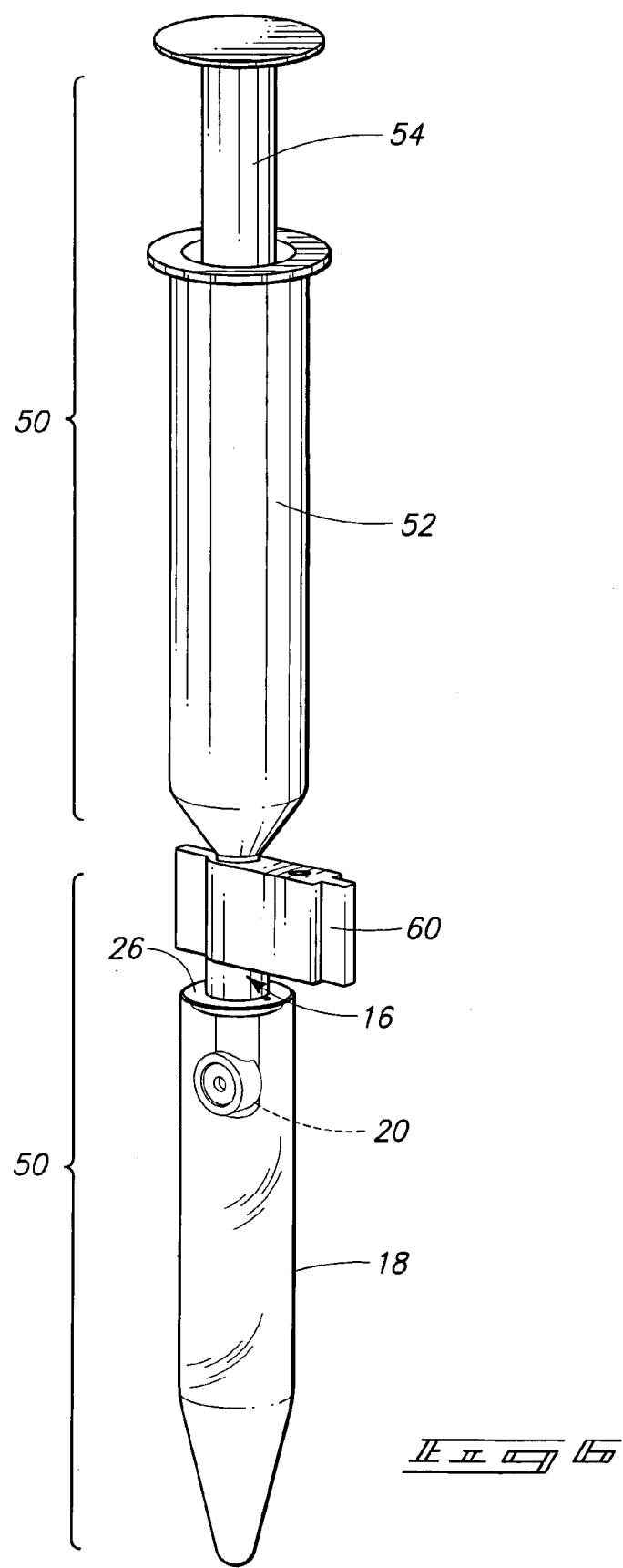

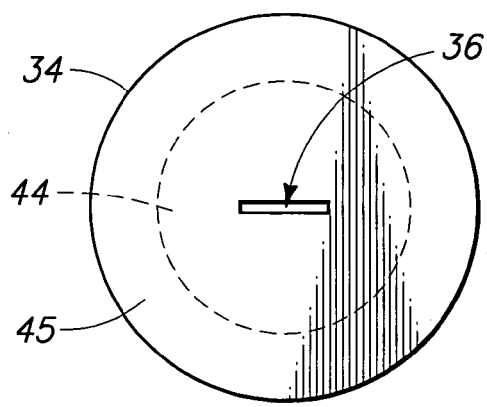
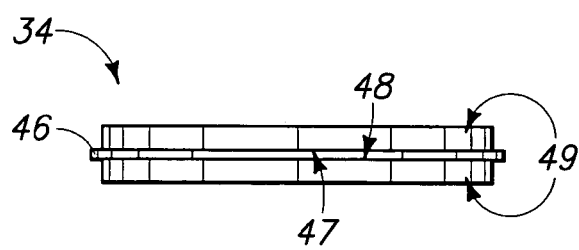
| Fig. 9A |
| Fig. 9B |
Fig. 9

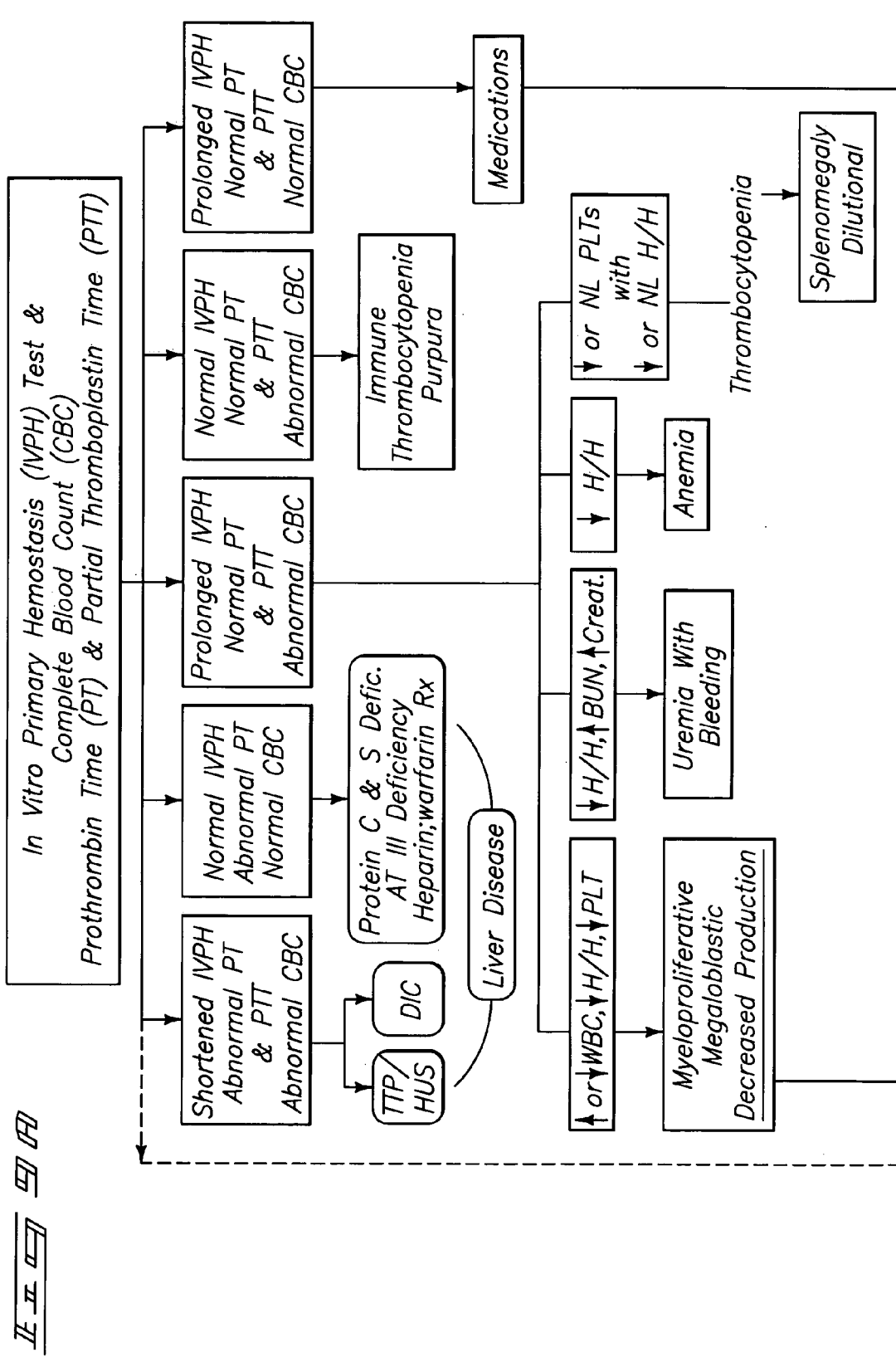

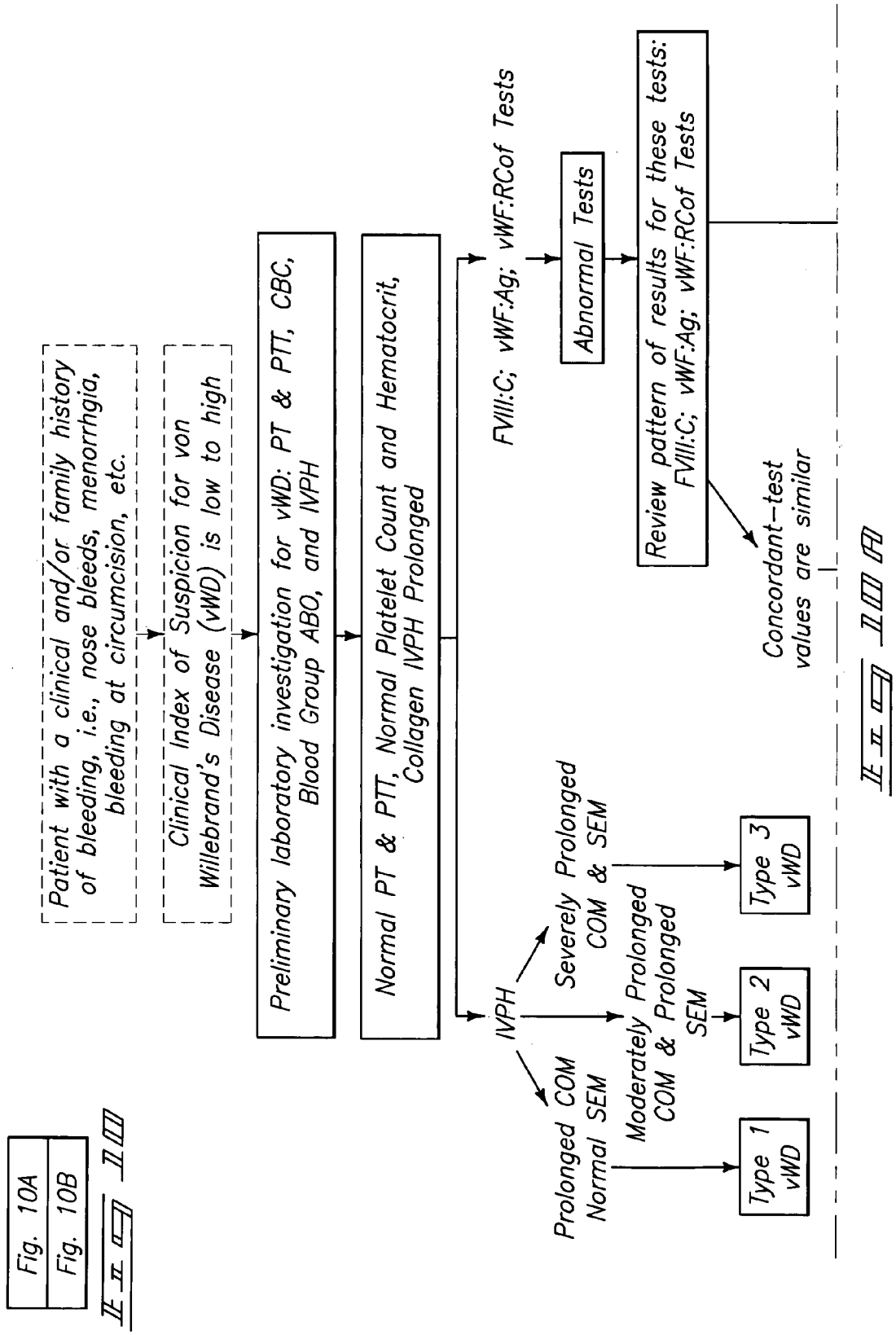

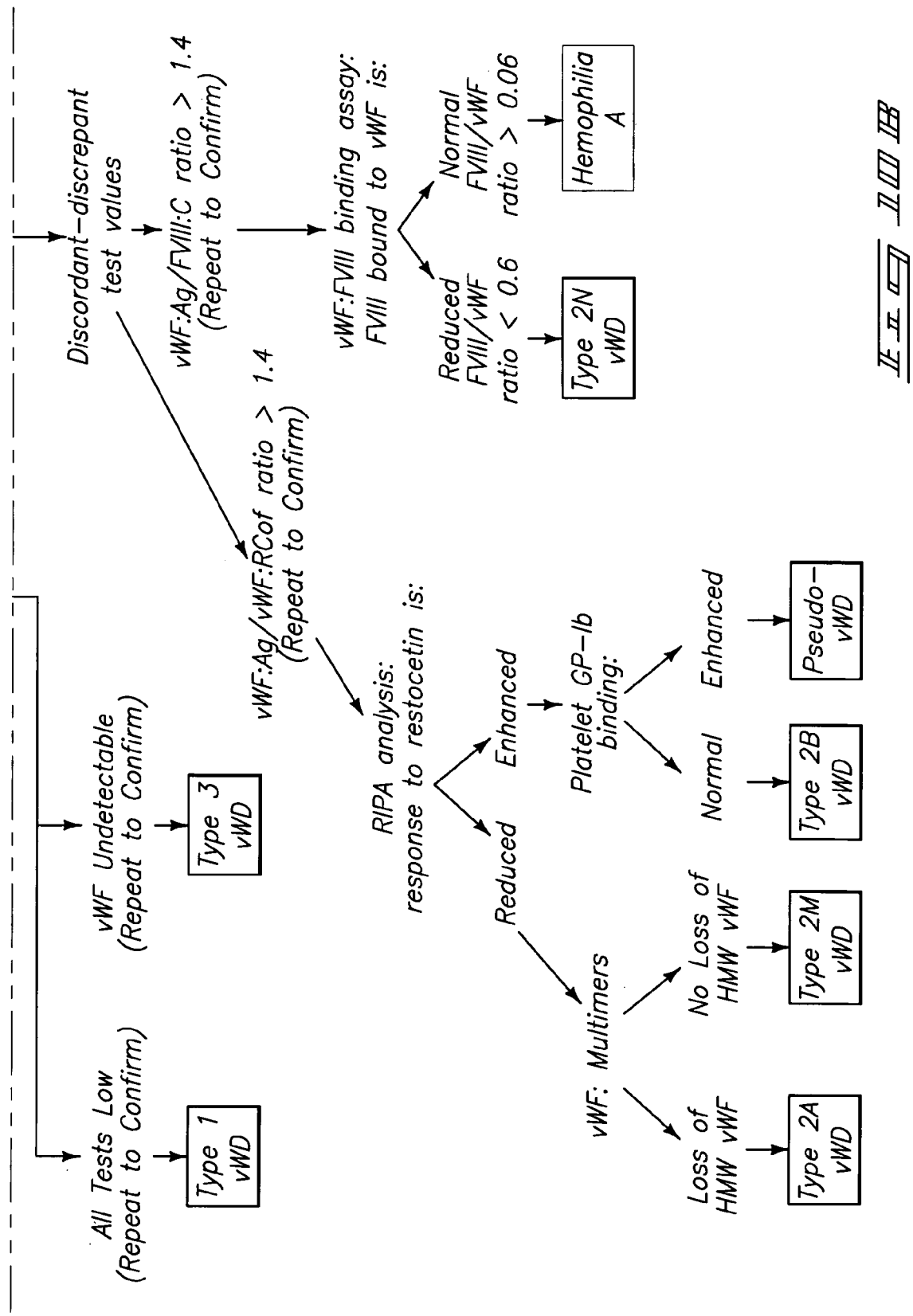

SYSTEM AND METHOD FOR IN VITRO BLEEDING TIME TESTING

RELATED PATENT DATA

This patent claims benefit of priority under 35 U.S.C. §119 to U.S. Provisional Patent Application Ser. No. 60/439,186, which was filed Jan. 10, 2003.

TECHNICAL FIELD

The invention pertains to an in vitro bleeding time determination device, a blood coagulation analysis system, and methods for analyzing blood coagulation.

BACKGROUND OF THE INVENTION

Blood coagulation, clot formation and hemostasis involve a complex multi-step system. Two biochemical pathways, referred to as the intrinsic pathway and the extrinsic pathway are involved in the complex system. In conjunction, the two pathways, each involving numerous protein factors, play a major roll in the control of blood clot formation.

Typically, initiation of blood clot formation is triggered by injury. A series or 'cascade' of events which activate various protein factors involved in the two pathways leads to the formation of fibrin from the precursor fibrinogen. Fibrin crosslink formation and interaction with blood platelets which have become activated due to the injury event, form a clot or "insoluble fibrin", which comprises aggregated platelets and interwoven fibrin.

Where certain factors or events involved in the coagulation cascade are inhibited or blocked, blood clot formation can be impaired leading to prolonged bleeding times. A number of medical conditions related to prolonged bleeding times have been shown to be associated with impairment of cascade events. Impairment can be due to an insufficiency, absence or overabundance of an otherwise normal coagulation factor, can be due the presence of one or more factors having decreased or no activity, or due to the effect or interference of medications or other agents.

A variety of tests have been developed to measure coagulation efficiency. An in vivo test known as the bleeding time test, has been used extensively. The bleeding time test involves forming small cuts on a patients arm and measuring the time it takes for the bleeding to stop. Due to numerous non-uniformities, such as incision direction, depth and length, and large potential for operator inconsistencies, the bleeding time test is often imprecise or inaccurate. The bleeding time test can also cause scarring and is not conducive to monitoring a blood condition over long periods of time.

In vitro tests have been developed that can provide information about certain general aspects of the coagulation cascade. One such test is the prothrombin time (PT) which measures the extrinsic pathway. Another is the partial thromboplastin time (PTT) tests the intrinsic pathway.

Additional test methods have been developed that study platelet aggregation. These tests typically utilize one or more aggregation inducing or enhancing agent (e.g. ADP, collagen, epinephrine and ristocetin) to study the ability of platelets to aggregate. However, since the ability of platelets to aggregate is only one aspect of clot formation, platelets studies, provide limited information regarding physiological clot formation. Similarly, platelet adhesion tests, which measure the ability of platelets to adhere to foreign materials such as glass, also provide limited information, can be very inconclusive and can produce unpredictable results.

It would be advantageous to develop in vitro hemostasis testing that more accurately simulates events at the site of a wound. It would additionally be advantageous to develop tests for detecting insufficiencies related to specific clotting factors and/or platelet factors.

SUMMARY OF THE INVENTION

The invention pertains to an in vitro bleeding time determination device which includes a sheet of material having a sheet thickness and an inner region surrounded by a peripheral region. The inner region has an opening which spans the thickness of the sheet. At least a portion of one side of the sheet of material contains a coating which includes collagen type I, fibrinogen, fibronectin, and von Willebrand factor, and which lacks type IV collagen.

In one aspect the invention includes a blood coagulation analysis system. This system includes a receiving device which has an internal chamber for receiving a blood sample and has an inlet in fluid communication with the internal chamber. The device has a single outlet in fluid communication with the internal chamber. A sensor is configured to detect fluid pressure and/or flow rate within the internal chamber. A sheet of material is associated with the outlet and is configured to span a flowpath through the outlet. The sheet of material has an opening spanning a thickness of the sheet. A controller is configured to receive pressure and/or flow information from the sensor and to regulate pressure and/or flow within the internal chamber.

In one aspect the invention pertains to a method for analyzing blood coagulation. A device is provided which has an internal chamber and an inlet port in fluid communication with the internal chamber. The device has a single outlet in fluid communication with the internal chamber. A source or a sample of blood is provided in selective fluid communication with the internal chamber through the inlet port. A sensor is disposed in pressure and/or flow rate sensing relation relative to the internal chamber. A sheet of material is provided spanning a cross-section of the outlet, the sheet of material having a single opening providing fluid passage through the sheet. Blood flow is initiated from the source into the device and pressure and/or flow information is routed from the chamber through the sensor to a controller. A clot blockage of the opening is formed and the controller is utilized to control pressure and/or flow within the internal chamber by controlling the flow rate from the source through the inlet port during clot formation.

BRIEF DESCRIPTION OF THE DRAWINGS

Preferred embodiments of the invention are described below with reference to the following accompanying drawings.

FIG. 6 is a perspective view of the tester assembly shown in FIG. 2 attached to a source syringe.

FIG. 7 is a plan view of a coated sheet according to an aspect of the invention.

FIG. 8 is a cross-sectional view of the coated sheet of FIG. 7.

FIGS. 9, 9A and 9B are diagrams depicting exemplary methodology for predicting blood conditions in accordance with one aspect of the invention.

FIGS. 10, 10A and 10B are diagrams depicting exemplary methodology for predicting blood conditions in accordance with a second aspect of the invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

This invention provides a device and system used to conduct in vitro bleeding time tests. The tester device replicates an injured or cut blood vessel. The tester device assembly and test system can be used to measure platelet plug formation (or primary homeostasis), platelet adhesion and/or platelet aggregation, clot formation, blood clotting times and/or to determine levels of specific blood clotting factors (individually or in combination). The tester device can be disposable and can be mass-produced for use in the apparatus and system described in this patent.

Figure 1:
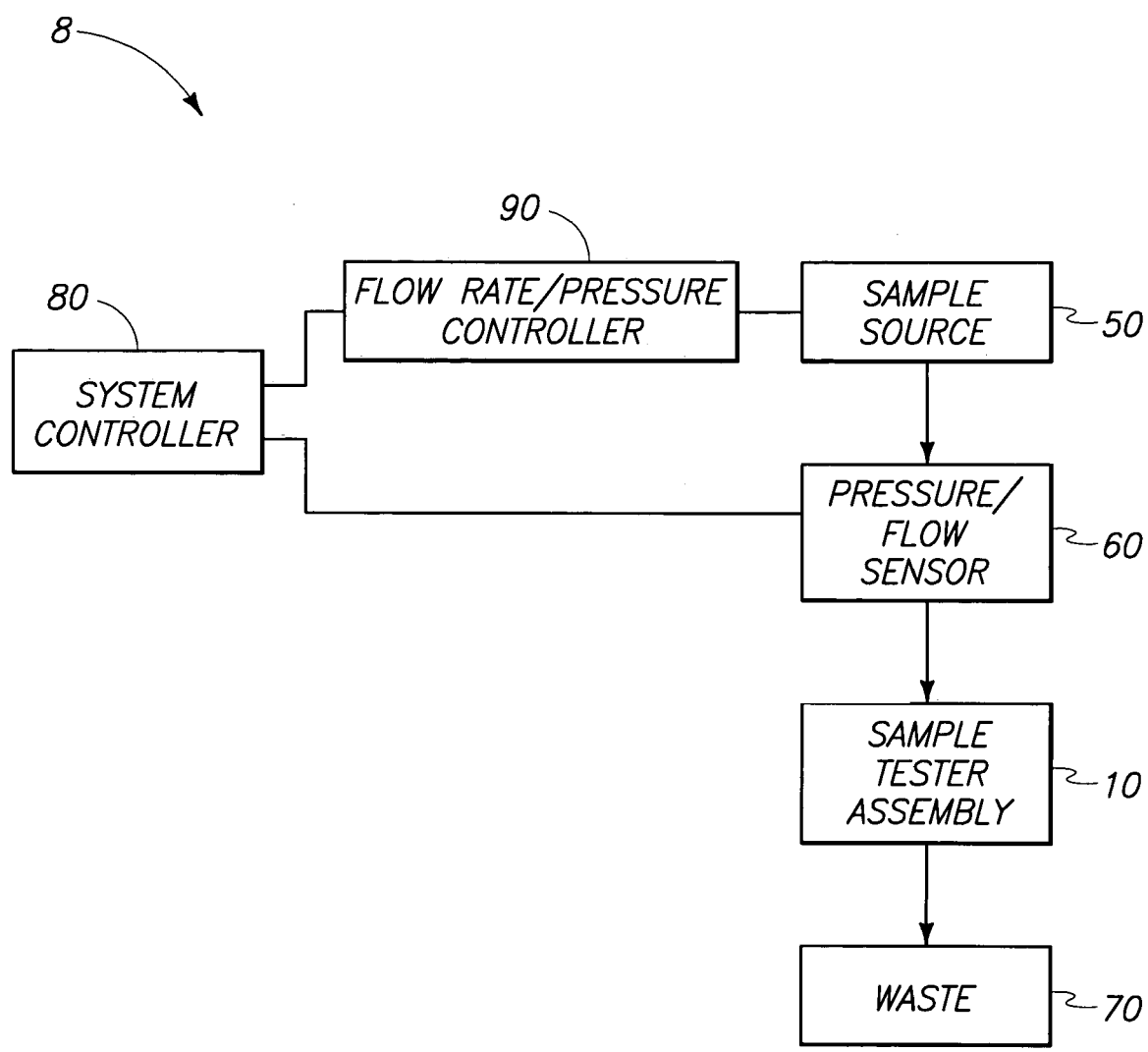
FIG. 1 is a flowchart diagram illustrating a system in accordance with a particular aspect of the invention.

A system 8 in accordance with an aspect of the invention is described generally with reference to FIG. 1. System 8 can be utilized for analyzing blood coagulation by measuring a bleeding time. The measurements obtained utilizing system 8 can determine or can assist in determining whether a blood sample obtained from an individual exhibits a shortened bleeding time, a normal bleeding time, or a prolonged bleeding time. For purposes of the present description, the term 'normal' can refer to a level or to a measurement, such as a bleeding or a coagulation time, that is within a range typically associated with individuals or populations that are free of coagulation impairment and/or whose blood coagulation is not currently influenced by medication or agents administered to promote or inhibit blood coagulation. In particular contexts, the term 'normal' can refer to a measurement or level within a range that is typical for a given individual. The term "prolonged" can refer to a bleeding time that is increased relative to levels typically considered to be normal. In some aspects the term "prolonged" can refer to an increased bleeding time exhibited by an individual relative to a lower time that has been measured for the subject individual. Similarly, the term "shortened bleeding time" can refer to a bleeding time that is short relative to a time range considered to be normal, or shortened relative to a bleeding time previously measured for the subject individual.

System 8 can also be utilized to monitor coagulation ability and/or bleeding time during various medical procedures and/or treatments. The results of testing utilizing system 8 can provide an independent determination or can be combined with one or more conventional testing techniques such as prothrombin time (PT), partial thromboplastin time (PTT), platelet aggregation, platelet adhesion, in vivo bleeding time, complete blood count (CBC), blood group (e.g. ABO), factor VIII coagulant (FVIII:C), von Willebrand antigen (vWF:ag), von Willebrand ristocetin cofactor (vWF:Rcof), von Willebrand factor collagen binding activity, high molecular weight multimers (HMW), or ristocetin-induced platelet aggregation (RIPA) tests.

In certain aspects system 8 can be utilized to detect a decreased activity, a decreased abundance or an absence of one or more coagulation factors in a blood sample obtained from an individual. Accordingly, system 8 can be utilized to detect, predict or diagnose, classify or monitor (or to assist in detection, prediction, monitoring, classification or diagnosis of) various blood conditions, including but not limited to, various forms of von Willebrand disease, various forms of anemia, proper or improper medication levels, immune thrombocytopenia purpura, various forms of thrombocytopenia, abnormal platelet aggregation, uremia, liver disease, congenital platelet defects (e.g. Glanzmann's thrombasthenia; Bernard Soullier's disease), thrombotic thrombocytopenia purpura/hemolytic uremic syndrome and disseminated intravascular coagulation. Such testing can be invaluable for pre-surgical blood screening as well as for diagnostic and monitoring purposes.

Blood coagulation analysis system 8 can include a sample tester assembly 10 as shown in FIG. 1. Assembly 10 can comprise a receiving device (described below) configured to receive a blood sample from a sample source 50. Sample source 50 can preferably comprise a blood sample obtained from an individual. Blood can be flowed from sample 50 into sample tester assembly 10 and in particular applications a sensor 60 can be provided to detect pressure and/or flow rates in the sample tester assembly.

Figure 2:
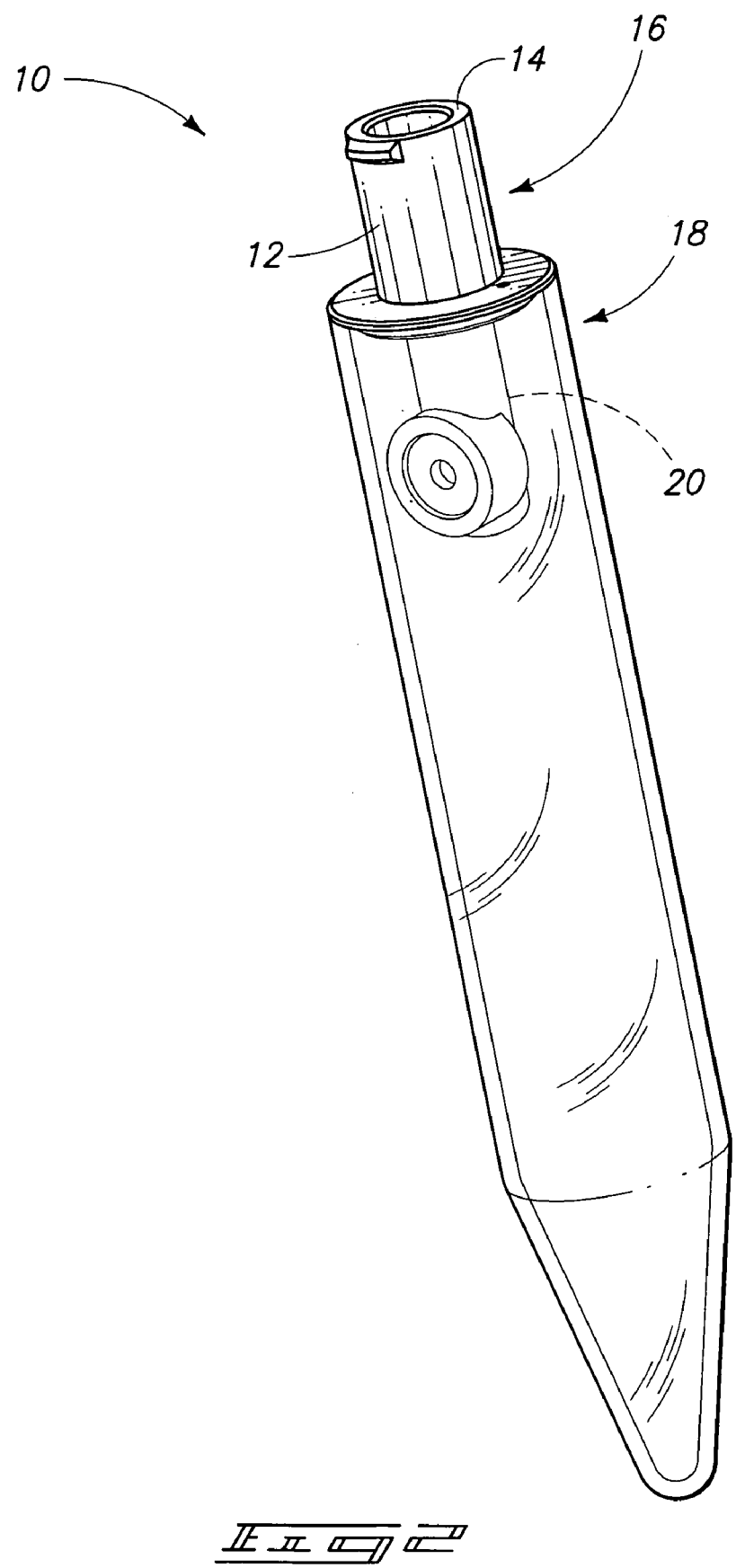
FIG. 2 is a perspective diagram of a tester assembly according to one aspect of the invention.

Tester assembly 10 is described in more detail with reference to FIGS. 2–5. Referring initially to FIG. 2, assembly 10 can comprise a receiving device 12. The receiving device can comprise a housing 14 having a first portion 16. Receiving device 12, also referred to as a testing device, can be utilized in conjunction with a collection vessel 18 and can be configured such that first portion 16 is disposed externally to vessel 18 and a second portion 20 is inserted internally into collection vessel 18. Housing 14 can be formed of a variety of materials. The housing of device 12 is preferably formed utilizing a material to which blood and blood components negligibly or minimally adhere. Exemplary materials for housing 14 include polycarbonate or other plastics.

Collection vessel 18 is not limited to a particular type of vessel and can be, for example, a glass or plastic vessel such as a conical vial or a test tube. It can be preferable that assembly 10 be fully disposable such that upon completion of testing of a blood sample, the entirety of assembly 10 can be disposed or as a single unit. The disposability of unit 10 can be advantageous for minimization of risk of contamination by blood products.

Figure 3:
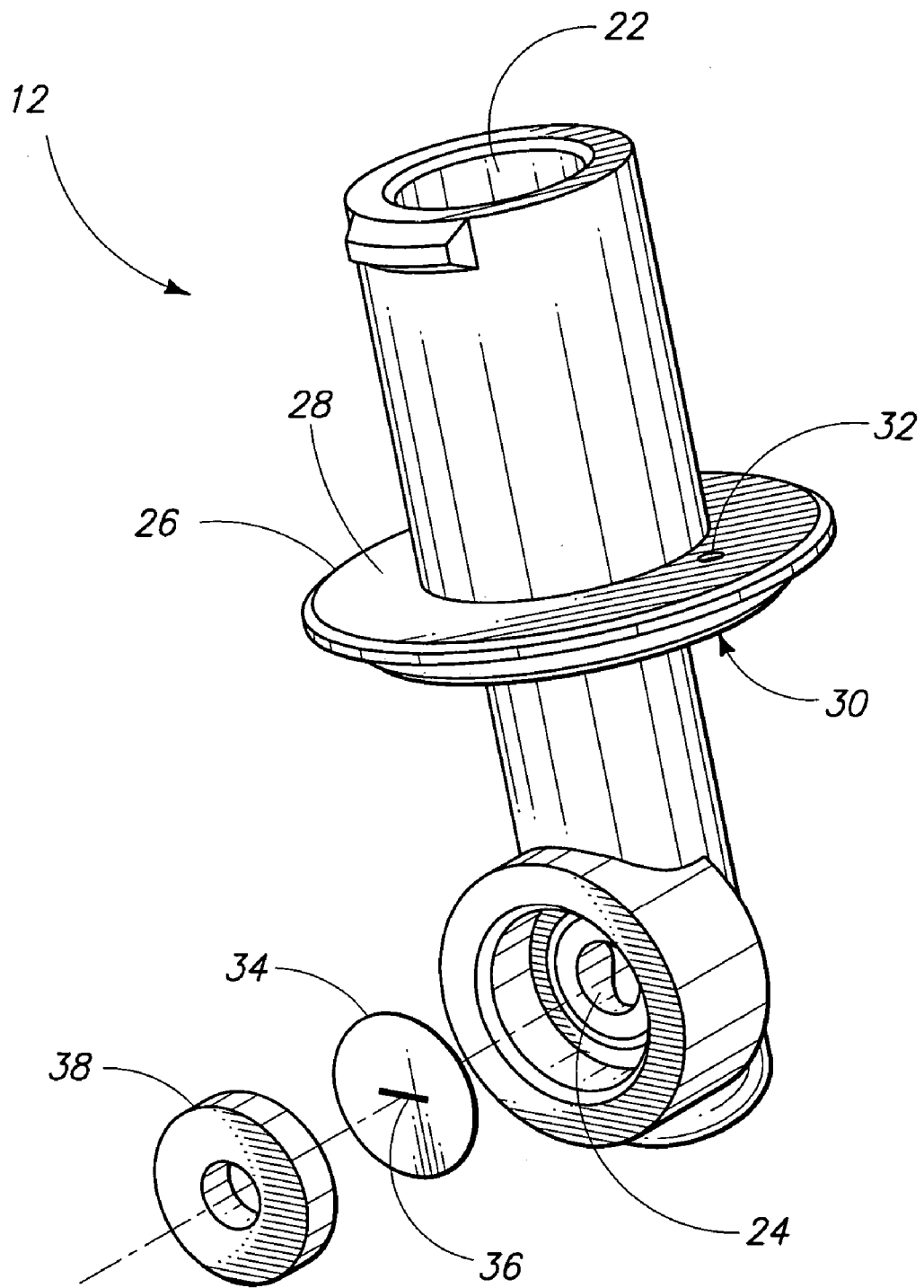
FIG. 3 is an exploded view of a tester device according to one aspect of the invention.

Referring to FIG. 3, such shows an exemplary configuration of test device 12. Housing unit 14 can have an inlet 22 and an outlet 24. Device 12 can also have a lip or projecting edge 26 having a lower surface 30 and an upper surface 28 and having at least one vent opening 32 which spans the thickness of lip 26. Device 12 can further include a sheet of material 34 having a single opening 36 through the sheet. As shown in FIG. 3, housing 14 can be fabricated such that sheet 34 is insertable into an outer portion of outlet 24. Preferably, sheet 34 spans a cross-sectional of outlet 24, thereby spanning the flowpath through the outlet. It can be preferable that sheet 34 be sealably seated within outlet 24 such that fluid passing into device 12 through inlet 12 exits solely through opening 36. As shown in FIG. 3, one method of seating sheet 34 can utilize an O-ring 38.

Although device 12 is depicted as having a cylindrical housing with a circular inlet and circular outlet, it is to be understood that alternative configurations are contemplated utilizing various shaped housings and openings. Accordingly, membrane 34 can comprise a circular shape as shown, or can comprise an alternative shape as appropriate for alternative outlet designs. Similarly, O-ring 38 can be formed to have a shape such that it can be inserted within opening 24 to sealably seat sheet 34 within the outlet. Additionally, although device 12 is shown having sheet 34 inserted within outlet 24, the invention contemplates utilizing alternative configurations, for example where membrane 34 is seated externally to housing 14 and is mounted utilizing, for example, an outlet cap (not shown).

In particular implementations of the invention, it can be preferable that opening 36 be a rectangular slit. Membrane 34 can be disposed spanning outlet 24 to have slit 36 in any directional alignment relative to the long axis of housing 14. However, it can be preferable that slit 36 be aligned substantially identically within each device assembly fabricated to minimize variation between devices and promote direct comparability between tests. Additionally, it can be preferable that slit 36 be aligned within opening 24 to be substantially perpendicular to the long axis of housing 14. The configuration of assembly 12 having slit 36 aligned perpendicular to the long axis of housing 14 can be referred to as the perpendicular alignment. It is to be noted that the perpendicular alignment is preferred in embodiments of the invention where sample testing is conducted with device 12 in a fully vertical position (having surface 32 of lip portion 26 substantially horizontal). Conducting tests with device 12 in the substantially vertical position places sheet 34 in a substantially vertical alignment which can minimize deformation of the sheet and/or the slit opening during testing. Alternatively, where device 12 is other than substantially vertical during testing, the perpendicular alignment can be utilized or sheet 34 can be inserted into opening 24 such that slit 36 is horizontal, or alternatively, slit 36 can be disposed in alternative alignment relative to the long axis of housing 14.

Figure 4:
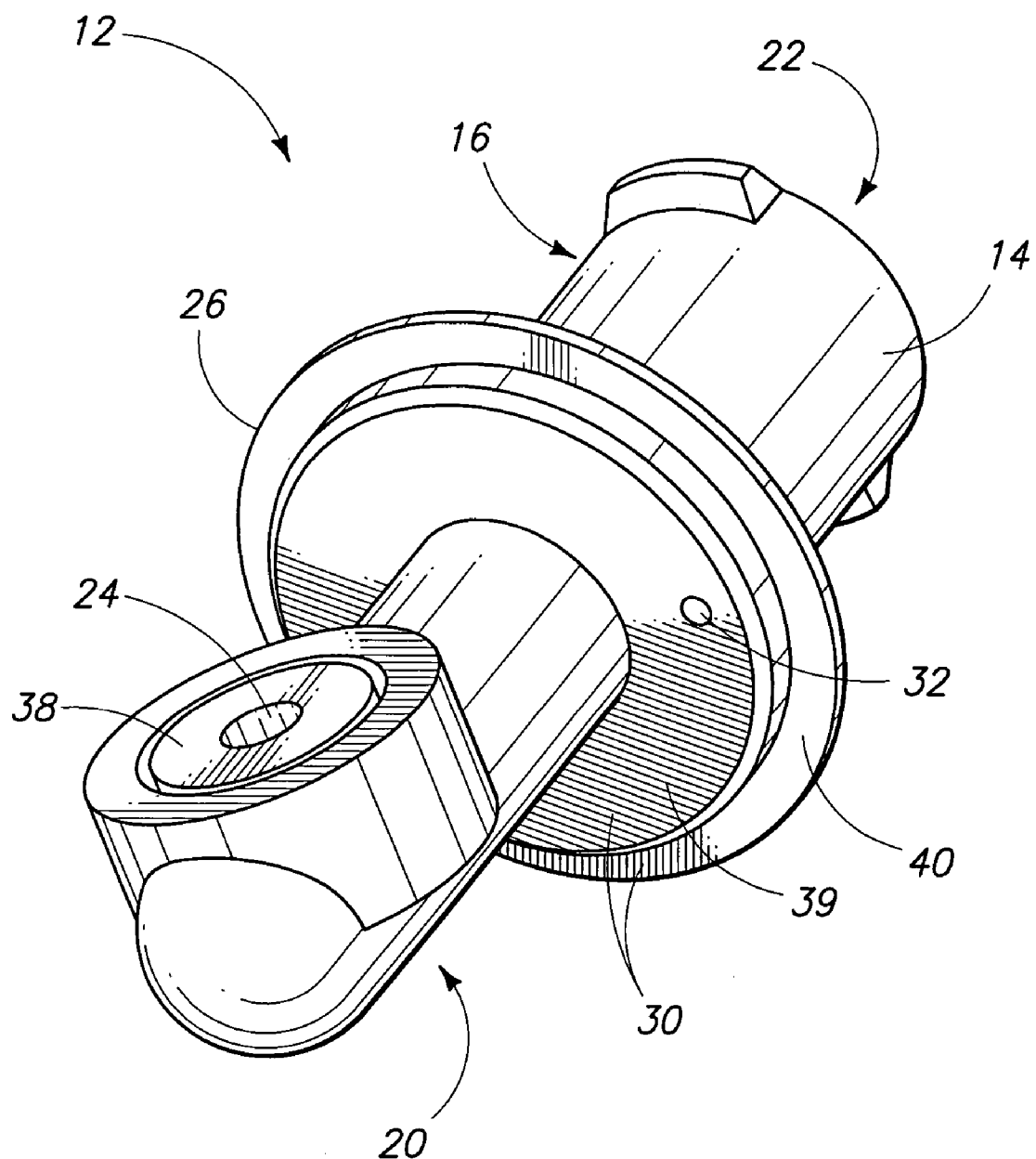
FIG. 4 is a perspective view of the assembled form of the tester device shown in FIG. 3.

Referring to FIG. 4, such shows testing device 12 in assembled form. Device 12 can be described as having a main body of housing 14 including an external portion 16 and a portion 20 which can be inserted into a collection vial such as vessel 18 shown in FIG. 2. In addition to the main body, housing 14 can include a projecting edge or lip portion 26 having a vent opening 32 which passes through lip 26. As shown in FIG. 4, lip portion 26 can have an inner diameter region 39 and a peripheral region 40. Lip region 26 as shown in FIG. 4 is an exemplary configuration where inner diameter region 39 has a thickness that is greater than external region 40 such that a portion of internal region 39 can be inserted within a collection vessel. It can be preferable that outer region 40 of surface 30 contact an upper surface of a collection device. Peripheral region 40 of surface 30 can preferably be sealable with (blocks fluid passage through) the contacting area of the collection vessel.

Although lip 26 is shown in FIG. 4 as having an outer periphery 40 which is thinner than inner region 39, it is to be understood that alternative embodiments are contemplated wherein lip 26 has a uniform thickness and/or wherein the entirety of lower surface 30 is on a single plane.

As shown in FIG. 4, lip portion 26 can have a single vent opening 32. Alternatively, two or more openings can be provided (not shown). Vent opening 32 is not limited to a particular shape and can be, for example, circular as shown. The location of vent opening 32 is not limited to any particular site within lip region 26. In some aspects, it can be preferable that vent 32 be disposed at a peripheral edge of lip 26 for ease of fabrication. An exemplary peripheral vent can have a U-shaped configuration having the arc of the U-shape radially inward and extending to the outermost edge of lip 26 (not shown).

Figure 5:
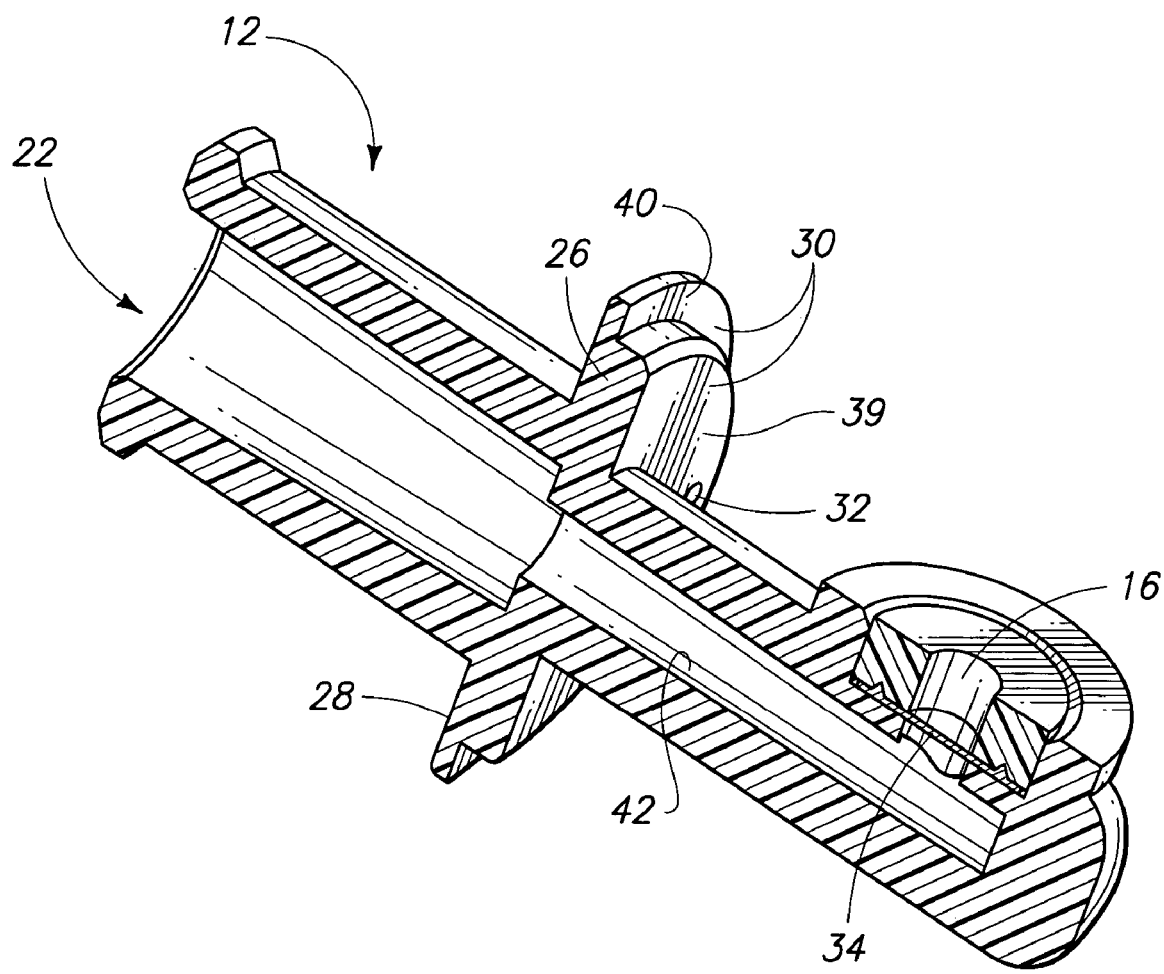
FIG. 5 is a cross-sectional view of the tester device taken along lines 5—5 of FIG. 4.

Referring to FIG. 5, device 12 has as internal chamber 42 for receiving a blood sample. Chamber 42 is in fluid communication with inlet 22 and with outlet 24. It can be preferable that device 12 be configured to have a single outlet from chamber 42 to allow pressure sensing and pressure control within the chamber (discussed below). As shown in FIG. 5, sheet 34 can be disposed such that the sheet spans the flowpath through outlet 24. Such configuration allows blood to exit device 12 preferably exclusively through the opening(s) in sheet 34. When the opening(s) in sheet 34 becomes blocked due to clot formation, for example, a resulting change in pressure or flow within chamber 42 can be detected and can be utilized for indication of formation and/or completion of a clot blockage of the opening(s) through sheet 34.

Referring again to FIG. 1, sample tester assembly 10, which can include the tester device assembly connected with the collection vessel, can be disposed of as a single unit to an appropriate waste 70. Sample source 50 can comprise a blood sample obtained from an individual. Sample source 50 can be disposed in fluid providing relation relative to the receiving device of sample tester assembly 10. A sensor 60 can be disposed between separate sample source 50 and sample tester assembly 10 to receive pressure information and/or flow rate information from the internal chamber of the tester device. This pressure and/or flow information can be routed to a system controller 80 which can be, for example, a computer.

The system controller can in turn control the pressure and or flow within the sample tester utilizing, for example, a flow rate controller 90. The particular type of unit utilized for flow rate controller 90 can depend upon the particular configuration of sample source 50. In particular instances, sample source 50 can be a pump system and controller 90 can be a pump controller. Controller 90 and sample source 50 can be independent, or can be integrated into a single unit (not shown). Similarly, system controller 80 and flow rate controller 90 can be integrated into a single unit (not shown) or can be independent.

In particular instances, sample source 50 can comprise a syringe and flow rate controller 90 can comprise a syringe drive. This aspect of the invention is described with reference to FIG. 6. Tester assembly 10 can be attached to a syringe 50. Syringe 50 can comprise a barrel portion 52 for holding and providing a blood sample into device 12, and a plunger 54. Flow into device 12 can be controlled by controlling descent of plunger 54 through barrel 52 utilizing controller 90 comprising, for example, a syringe drive.

Pressure within the internal chamber of device 12 can be monitored by sensor 60 disposed between syringe 50 and device 12. Alternatively, sensor 60 can comprise a flow rate sensor. In particular applications, sensor 60 can comprise both a flow rate sensor and a pressure sensor, either as independent units (not shown) or as an integrated sensor unit Blood exiting device 12 is collected within collection vessel 18. System 8 shown in FIG. 1 can be configured such that an increased pressure corresponding to blockage of the outlet of device 12 due to clot formation across the opening through the sheet of material results in cessation of flow. System 8 can further be configured such that the time between initiating flow into device 12 and the cessation of flow due to blockage by clot formation is measured as the resulting bleeding time for the particular sample.

In particular aspects, it can be preferable that conditions within the internal chamber of device 12 be maintained within a range of flow rate or at a particular pressure. In order to predict in vivo coagulation events, it can be preferable that the internal chamber pressure be maintained at or near a physiological range or specific physiological value. Accordingly, it can be desirable to maintain the pressure with chamber 42 at a pressure of from above 0 mmHg to less than or equal to about 300 mmHg. In some applications it can be preferable to maintain the pressure at or above 10 mmHg and below 200 mmHg, and in particular instances the pressure can be maintained at a substantially constant pressure of from about 5 mmHg to about 80 mmHg.

Physiological vascular wall shear rates can range from about 30 $sec^{-1}$ to about 10,000 $sec^{-1}$, depending in part upon vascular diameter. Physiologically mechanisms of primary hemostasis (initial platelet plug formation) and clot formation can be affected by shear forces. Additionally, the effects of particular clotting factors, and the effectiveness of various medications or agents utilized to treat blood conditions or affect clotting events can be influenced by shear. Since shear forces depend upon pressure and flow rate, it can be preferable to monitor and/or control the flow rate of blood through device 12. Flow rate through device 12 can be, for example, from about 1 ml/min to about 10 ml/min. Additionally, device 12 can be utilized at various predetermined flow rates and/or pressure ranges to simulate particular in vivo shear conditions. A specified shear force can be achieved and/or maintained by controlling pressure and flow within device 12. Because parameters such as pressure, flow and shear can affect rates and/or ability of coagulation events, it can be useful to perform tests utilizing a variance of these parameters. Accordingly, a series of independent tests can be conducted under altered pressure and/or flow rate (preferably within physiological range). A comparison of results obtained under varied flow/pressure parameters and/or comparison to typical or normal results can assist in predicting or identifying particular blood conditions.

Referring next to FIG. 7, such shows an exemplary sheet 34 which can be utilized for conducting blood coagulation and bleeding time analysis in accordance with the invention. Sheet 34 can comprise a radially inner portion 44 and a peripheral portion 45 surrounding inner portion 44. The relative areas of inner portion 44 and peripheral portion 45 are not limited to specific values. Peripheral portion 45 can correspond to a portion of sheet 34 which comes in contact with, or is covered by a portion of the housing of the tester device. Sheet 34 has opening 36 with inner region 44. Opening 36 can preferably comprise a slit shape as shown. However, the invention contemplates utilizing more than one opening and/or alternate opening shapes. Alternate shapes which can be utilized for opening(s) 36 include, for example, circular, square or irregular shapes. Where more than one opening is utilized, the openings can be dispersed across inner region 44 or can be aligned to form one or more rows of openings. It can be preferable to have a single opening such that formation of a single clot can block the opening and bleeding time can be determined for an individual test based upon formation of a single clot.

Because the opening size and shape can affect shear, it can be advantageous to provide an appropriate opening size and shape which can promote shape and dimension consistency during performance of the test. It can be additionally advantageous to provide a sheet 34 having a single opening of a size which is precisely reproducible from one sheet to the next which additionally maintains shape during testing to provide consistent, reliable and reproducible results. Accordingly, it can be preferable that sheet 34 have a single opening, and that the opening be a rectangular slit having a width of from about 60 microns to about 120 microns and a length of less than about 500 microns. More preferably, the slit length is from about 300 microns to about 400 microns. It can be advantageous to utilize the described rectangular dimensions to inhibit slit widening and/or buckling.

Referring to FIG. 8, such shows a cross-section across a thickness of sheet 34. Sheet 34 can comprise a substrate material 46 having a first surface 47 and an opposing surface 48. Substrate material 46 can comprise a thickness of from about 0.1 mm to about 0.2 mm, and can preferably be about 0.15 mm thick. Sheet 34 can additionally comprise a coating material 49 which, in some aspects, can be across an entirety of surface 47 and across an entirety of surface 48 as shown in FIG. 8. Alternatively, a portion or an entirety of a single side of substrate material 46 can contain coating mixture 49. Preferably, at least inner diameter region 44 (FIG. 7) of first side 47 contains coating material 49, where first side 47 will be disposed facing the internal chamber of the testing device. More preferably coating mixture 49 is applied to at least a portion of each side of substrate 46. Sheet 34, containing the substrate and coating, can have a thickness of 0.3 mm to about 0.6 mm, and in particular applications can preferably have a thickness of about 0.45 mm.

Substrate material 46 can comprise a non-porous material or can comprise a porous material, at least initially (prior to applying coating material 49). Exemplary materials which can be comprised by substrate 46 include, but are not limited to, nitrocellulose, cellulose acetate, PVDF hydrophobic membranes, and nylon materials such as nylon membrane materials. In one embodiment, substrate 46 can be a nylon membrane having a pore size of approximately 3–10 microns. In some aspects a preferred opening size can be from about 6 microns to about 8 microns, and in particular embodiments the pore size is 8 microns. It can be advantageous to utilize a nylon membrane material having a relatively large pore size relative to alternative materials such that when the membrane is coated with a coating mixture in accordance with the invention (discussed below) the coated membrane material can more accurately duplicate a vessel wall. For coating purposes, it can be advantageous to utilize a nylon material with a high ratio of amine groups relative to carboxylate end groups to enhance protein adhesion to the nylon material. An exemplary nylon material which can be utilized for substrate 46 is NOVYLON® (Cuno Incorporated, Meriden, Conn., USA).

Coating material 49 can comprise a substance or a mixture of substances which can initiate, activate and/or enhance on or more of platelet adherence, platelet aggregation, platelet plug formation and blood clot formation. Coating material 49 preferably comprises collagen. Because platelets present in blood can adhere to particular types of collagen while other types of collagen such as type IV collagen show decreased or negligible ability to adhere to platelets, it can be advantageous to exclude collagen types such as type IV from coating material 49. Additionally, to simplify results analysis and to simplify preparation of the vessel wall simulating sheet, it can be advantageous to use a single type of collagen, such as collagen type I, within coating material 49. It is to be understood, however, that the invention contemplates utilizing one or more additional or alternative types of collagen that are capable of platelet adhesion, for example collagen type II and/or collagen type III.

In particular instances, coagulation analysis and/or bleeding time determination according to the invention can be conducted utilizing a so called "collagen only membrane". The collagen only membrane can comprise nylon membrane which has been at least partially coated with a coating mixture containing collagen type I and where the mixture lacks any additional coagulation factors or other agents known to affect coagulation.

An exemplary collagen only membrane encompassed by the invention can be prepared as follows. A 25 cm×20 cm total surface area of nylon membrane is flooded with 20 mg/ml 1-cyclohexyl-3-(2-morpholinoethyl) carbodi-imide metho-p-toluenesulfonate (CDI) in distilled water (herein after referred to as CDI solution). The excess CDI solution is drained and the membrane is treated by adding 15 ml of a first collagen coating mixture, the first collagen coating mixture containing 40 grams of collagen I powder; 200 ml of CDI solution and 4 ml of glycerol.

Collagen I powder for preparation of the collagen only membrane is preferably a smooth powder of consistent size, the powder being free of clumps and having no powder particles greater than 0.5 mm. An exemplary collagen type I powder which can be utilized for purposes of the invention can be prepared from bovine Achilles tendon which is dried and ball milled a minimum of three times to produce the fine powder. An appropriate powder is currently obtainable from Sigma-Aldrich Company, St. Louis, Mo.

The 15 ml of the first collagen mixture is mixed onto the membrane and smoothed over the membrane surface. The membrane is then turned over onto a non-stick surface such as, for example, a Teflon coated or stainless steel surface. The membrane can then be smoothed from the top side to eliminate or reduce excess protein from the underside surface, reduce or remove any air bubbles, and provide a uniform coating across the surfaces of the membrane. An additional 15–20 ml of the first collagen mixture is added to the membrane. The additional first collagen mixture is mixed and smoothed onto the membrane as discussed above and the membrane is allowed to dry. Drying can preferably be conducted at a temperature of from about 40° C. to about 45° C.

After drying, one side of the coated membrane material can be treated with collagenase and heat treated for from about 1 hour to about 2 hours at a temperature of from about 40° C. to about 45° C. The collagenase treated membrane is then rinsed with saline or with saline containing protease inhibitor(s). After rinsing, the membrane is again dried (for example, overnight) at a temperature of from about 40° C. to about 45° C.

The coating process described preferably fills the pore openings such that an essentially non-porous membrane results, where essentially non-porous refers to an absence of detectable pores that are permeable to water.

The above coating process is described in relative amounts of surface area and reagents. The amounts can alternatively be scaled proportionally to treat substrate material of other areas. Appropriately sized and shaped sheets for use in a device in accordance with the invention can be cut from the substrate material prior to or after formation of the coating.

A slit opening can be formed in the collagen only membrane either prior to coating the membrane material or after coating formation. An exemplary method of forming the slit is to utilize a beveled and/or tooled punch, preferably precise to within 0.015 mm.

In alternative preparations, coating mixture 49 of FIG. 8 can additionally comprise one or more additional substances which can activate, assist in activating, enhance, stimulate or otherwise affect one or more of platelet plug formation, blood coagulation and/or clot formation. Exemplary substances include, but are not limited to, fibrinogen, von Willebrand factor, fibronectin or fibronectin fragments or peptides (including but not limited to Arg-Gly-Asp (RGD) peptides), prothrombin, thrombin, thrombin-receptor-activating peptide, ancrod, prekallekrein, high molecular weight kinninogen, reptilase, coagulation factor XII, activated coagulation factor XII, coagulation factor IX, activated coagulation factor IX, coagulation factor VIII, activated coagulation factor VII, activated coagulation factor VII, tissue thromboplastin, tissue factor/factor VII complex, phospholipids (e.g. rabbit brain cephalin, platelet activating factor (1-O-palmityl-2-acetyl-rac-glycero-3-phophocholine) and 3-O-palmityl-2-acetyl-sn-glycero-1-phosphocholine), integrins (e.g. glycoprotein IIb-IIIa), antibodies (e.g. anti-glycoprotein IIIb-IIIa), immunoglobulin superfamily molecules (e.g. platelet-endothelial cell adhesion molecule-1 (PECAM-1)), adenosine diphoshate (ADP), thromboxane, arachidonic acid, ristocetin, botrocetin, or recombinant forms of any of the listed protein factors and agents.

An example of material sheet 34 of FIGS. 7 and 8 having coating material 49 comprising coagulation promoting factors in addition to collagen type I can be referred to as a subendothelial membrane (SEM). Coating 49 for the SEM embodiment can contain, in addition to collagen type 1, von Willebrand factor, fibronectin and fibrinogen. An exemplary method for preparation of an SEM membrane is described below.

A cryoprecipitate is formed utilizing commercially available group A plasma. After freezing the plasma to form cryoprecipitate and thawing to about 4° C., the cryoprecipitate can be collected by centrifugation at about 4° C., and can optionally be combined with cryoprecipitate samples obtained from multiple donors. After collection and combination of the cryoprecipitate, the cryoprecipitate is maintained at approximately 4° C. without any additional freezing. Alternatively, the cryoprecipitate can be frozen for storage prior to use. An appropriate cryoprecipitate suspension or solution for utilization in preparation of the coating mixture described below can have the following protein concentrations: fibrinogen 400 to 600 mg/dL; von Willebrand factor 100 to 400 U/dL; and fibronectin content on the order of approximately 22 mg/ml. For purposes of the following description, this mixture will be referred to as the cryoprecipitate solution.

A concentrated mixture can be prepared as follows. 200 ml of CDI solution (20 mg/ml in water as described above) is stirred while slowly adding approximately 40 grams of collagen type I powder (described above) to produce a collagen/CDI mixture. 180 ml of the cryoprecipitate solution is slowly added to the collagen/CDI mixture and is mixed to form a fine slurry. The mixture can also be heated during preparation to a temperature of less than or equal to 45° C. Mixing can typically be conducted over a period of about 60 minutes. 4 ml of glycerol is then added with additional stirring at a temperature of less than or equal to 45° C. for about 60 minutes. This concentrated mixture can be used immediately or can be stored at a temperature of approximately 4° C. for a period of months.

A nylon substrate material can be coated to form an SEM as follows. The SEM preparation is described for a 25 cm×20 cm surface of a nylon membrane material. However, it is to be understood that the described treatment can be proportionally scaled for treatment of larger or smaller surface areas. Utilizing a 25 cm×20 cm surface area nylon membrane material, the material is flooded utilizing about 20 ml of CDI solution. 15 ml of the concentrated SEM solution is added and is mixed on the membrane and smoothed over the membrane surface. The membrane is then turned over onto a non-stick surface such as a Teflon coated surface or stainless steel surface. The membrane can smoothed from the top side to decrease or eliminate excess proteins from the undersurface, remove or reduce air bubbles, and to provide a uniform surface coating.

A second mixture is formed by combining 30 ml of the concentrated SEM mixture, 4 ml of the cryoprecipitate solution and 10 ml CDI solution. The second mixture is placed over the top side of the membrane and allowed to form a uniformed coating by for example, swirling and/or swishing. The membrane is then treated at a temperature of approximately 45° C. for up to about 5 days. Subsequently, 10 ml of the CDI solution is added over a first side of the membrane and a second 10 ml is added over the opposing side of the membrane to completely wet the membrane. Any excess CDI solution is drained immediately upon full wetting and a third mixture is added to the membrane. The third mixture is composed of 30 ml of the concentrated SEM mixture, 4 ml of the cryoprecipitate solution and from about 15 to about 20 ml of CDI solution. Upon addition of the third mixture, the membrane is swirled to produce a uniform coating and again incubated at a temperature of approximately 45° C. until dry or longer, up to about 1 week.

Slit formation and cutting to an appropriate size SEM can be as described above with respect to the collagen only membrane.

In addition to the collagen only membrane and SEM sheet materials produced above, one or more additional factors can be included in a coating mixture by, for example, adding one or more of the coagulation agents listed above during preparation of the described collagen only coating or the described subendothelial coating.

The coated sheets formed above can have thicknesses of from about 0.3 mm to about 0.6 mm. The coated sheet materials can be stored at room temperature and can be cut into appropriate shapes either prior to or subsequent to storage. Further, a sheet material which has been cut into an appropriate shape can be assembled into a testing device which can optionally include the collection vessel portion of the tester assembly (as shown in FIG. 2) prior to storage.

The test devices described above can be utilized to measure bleeding times. In particular instances the devices can be utilized to detect coagulation abnormalities, predict and/or diagnose one or more of decreased abundance, decreased activity or absence of one or more coagulation agents as compared to corresponding normal values, and/or to measure or monitor bleeding times prior to, during or after therapeutic or medical treatment or surgery.

Coagulation analysis of a sample of blood obtained from an individual in accordance with methodology of the invention can utilize one or more individual testing device where the individual testing devices have like or differing coating mixtures as described above. Additionally, multiple devices can be utilized to conduct independent tests under multiple pressure/flow conditions, for example to analyze effects of shear on primary hemostasis, clot formation and/or bleeding times.

Methodology for measuring bleeding time and/or analyzing blood clot formation in accordance with the invention is described referring again to FIG. 1. An exemplary test utilizing system 8 is described with a collagen only membrane in tester assembly 10. It is to be understood that the described method can also be used for any of the alternative coated sheet materials set forth above.

A blood sample source 50 such as a syringe can be provided with a blood sample obtained from an individual whose blood is to be tested. Pressure/flow sensor 60 can be mounted between syringe 50 and sample tester assembly 10. Blood flow from sample source 50 can be initiated into sample tester assembly 10. Blood flow from sample source 50 can be initiated into sample tester assembly 10 by flow controller 90. The initial flow rate can be, for example, from about 1 ml/min to about 10 ml/min. During the flow of blood from sample source 50 into sample tester assembly 10, the pressure and or flow rate within the internal chamber of the tester assembly can be detected by sensor 60. Sensor 60 can be configured to provide pressure information, flow rate information, or both, to system controller 80 which can in turn be configured to control or maintain a desired pressure and/or flow rate within the internal chamber by controlling flow rate from sample source 50 utilizing flow rate controller unit 90.

System controller 8 can additionally be configured to detect blockage of the slit provided in tester assembly 10 based upon pressure and/or flow information from sensor 60. Accordingly, system controller 80 can be configured to trigger a cease in flow into sample tester assembly 10 upon blockage of the slit opening. Measurement of the time lapse between initiating flow rate and ceasing flow into the sample tester can be recorded by controller 80 as the bleeding time for the specific blood sample across the collagen only type of membrane. System 8 can optionally be configured to allow visual and/or optical detection of the cessation of flow across the membrane.

The described bleeding time test can be conducted at a temperature of from about 30° C. to about 38° C. In order to maximize accuracy of indication and prediction of events that occur in vivo, it can be preferable that the testing to be conducted at or near physiological temperature. Accordingly, the blood sample can be provided at physiological temperature/and or maintained at physiological temperature through the testing device. A heater can be included in system 8 (not shown) and controller 80 can be configured to monitor and/or regulate the temperature during testing.

The collagen only membrane test described above can be repeated utilizing a second portion of the same sample or using a separately collected sample from the same individual to monitor or detect changes in bleeding time. Alternatively, the test can be repeated utilizing the method set forth above replacing the sample tester assembly with a sample tester assembly having an SEM type membrane or alternative membrane set forth above.

In particular applications, a series of tests can be performed on blood from a given individual utilizing a single type of membrane to monitor blood coagulation of an individual over time. These series of individual tests can be utilized, for example, to monitor a treatment therapy or to monitor effects of other medical treatments on bleeding time and coagulation ability.

Individual tests or series of tests can also be performed utilizing more than one of the types of membranes described above. The results obtained utilizing two or more membrane types can be compared to provide information regarding the ability of an individual's blood to coagulate. This method can be used to detect coagulation abnormalities and when combined the results can be used to predict or diagnose a deficiency in an amount or an activity of a particular coagulation factor or other coagulation agent in an individual.

In another aspect of the invention, an initial test or series of tests can be conducted as described above. Upon detection of a potentially abnormal condition, by for example obtaining prolonged coagulation times for one or more tests, additional testing can be conducted to further predict or narrow the possible causes of the abnormal condition. The additional testing can comprise utilizing membranes having added coagulation agents in the coating as described above. Alternatively, a sample of blood obtained from the affected individual can be provided and, prior to testing utilizing an SEM, a collagen only membrane, or both (independently), one or more blood coagulation agent can be added to the sample. Exemplary coagulation agents which can be added to the sample prior to performing the test include any of the agents set forth above with respect to optional coating components. A difference in bleeding time due to the addition of agent(s) to the sample (or membrane) can be utilized to determine or predict decreased activity or amount of a specific factor or factors in the blood of the individual relative to a normal level.

In particular instances, a first test can be conducted on a blood sample from an individual utilizing a first set of flow rate and pressure parameters to obtain a first bleeding time. A second test can be conducted on a blood sample from the same individual utilizing a second set of parameters where at least one of the pressure and the flow rate vary from the first test producing a second shear rate that is high relative to the first test. The bleeding times from the first and second test can be compared to each other and/or to test results obtained for normal individuals under correspondingly similar parameters. Such comparison can be helpful for predicting or identifying particular blood conditions. For purposes of the present description, a low shear rate can be less than or equal to about 1000 $sec^{-1}$, a high shear condition can be a shear rate of greater than about 1000 $sec^{-1}$, and very high shear can refer to a shear rate of greater than or equal to about 8000 $sec^{-1}$.

An exemplary application for testing under varied shear conditions is detection or identification of von Willebrand factor deficiencies. Because von Willebrand factor can have a larger role in primary hemostasis under relatively high shear, a decreased ability to form a platelet plug can occur under increased shear forces due to von Willebrand factor deficiency. Accordingly, a prolonged bleeding time obtained for a second test conducted under high shear relative to the first test conducted at low shear can be indicative of abnormal von Willebrand factor (either abundance or activity).

Results obtained utilizing the various described test methods can be combined with one or more conventional blood testing methods. The combination of methods and results can be useful for analyzing or predicting specific conditions. Exemplary test combinations and utilization of results for detecting, predicting or diagnosing specific disorders is shown in FIG. 9.

Figure 9B:
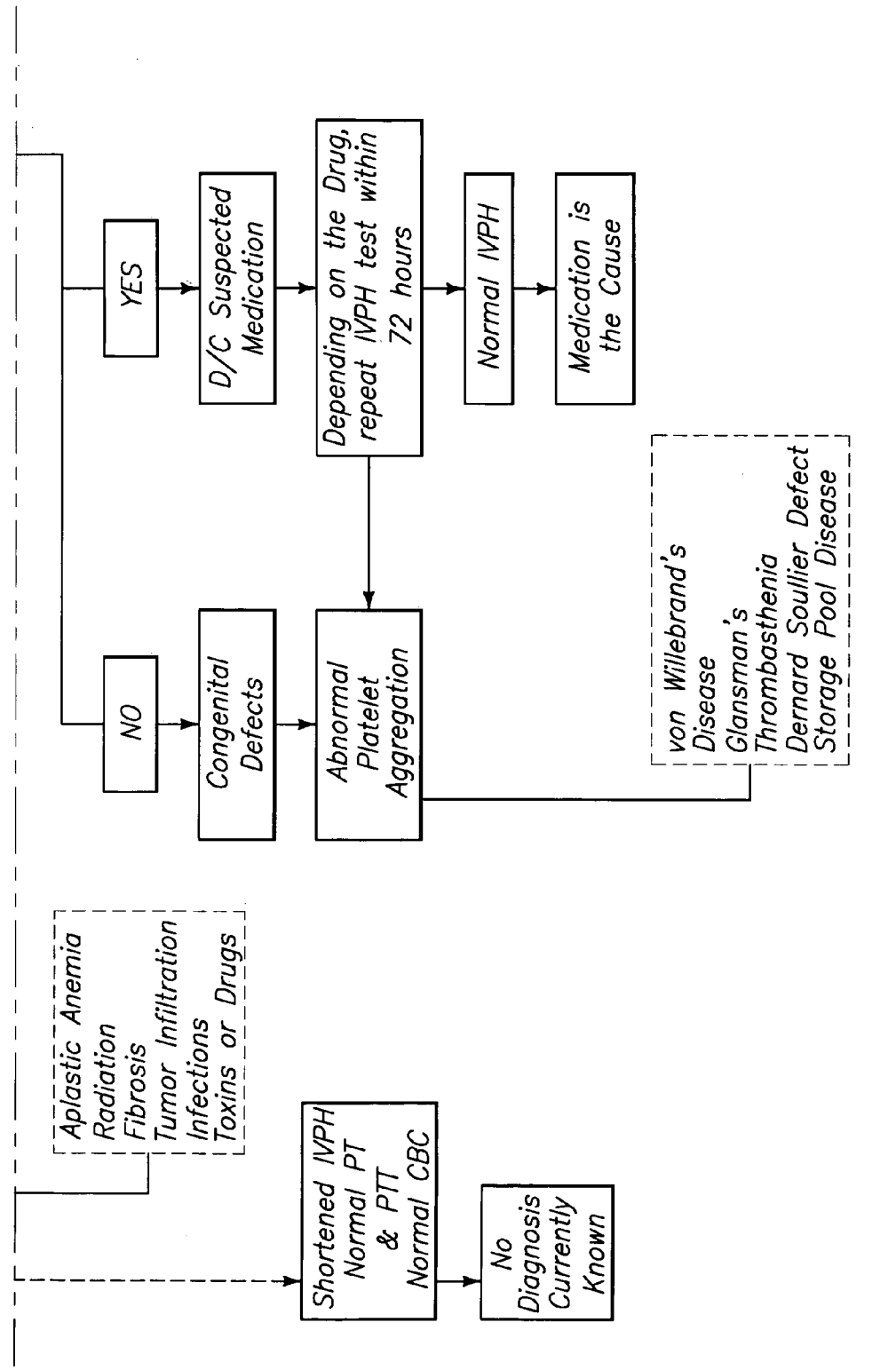

As shown in FIG. 9, results of tests utilizing the above described in vitro methods (also referred to as in vitro primary hemostasis (IVPH) tests) can be combined with results from one or more of prothrombin time (PT), partial thromboplastin time (PTT) and complete blood count (CBC) tests. The results of the tests can be combined and analyzed as diagrammed in the figure to predict or indicate various conditions. The various additional abbreviations in FIG. 9 are utilized as follows: TTP=thrombotic thrombocytopenia purpura; HUS=hemolytic uremic syndrome; DIC=disseminated intravascular coagulopathy; PLT=platelets; H/H=hemoglobin/hematocrit; WBC=white blood cell count, BUN=blood urea nitrogen; Creat.=creatinine; NL=normal; and AT III=antithrombin III. As shown, the various combinations of normal, prolonged and shorten time can be useful for predicting conditions such as congenital blood defects, abnormal platelet aggregation, effective or non-effective medication or levels of medication, anemia, etc.

In addition to the exemplary methods outlined in FIG. 9, testing in accordance with the invention can also be utilized for predicting or determining which of alternate types of von Willebrand disease is afflicting an individual. An outline of appropriate testing and analysis for the forms of von Willebrand disease is outlined in FIG. 10. As shown, by comparing results of tests performed utilizing the collagen only membrane with results utilizing the SEM, and, in some instances one or more additional test selected from PT, PTT, Blood group, ABO, CBC, Hematocrit, factor VIII coagulant (FVIII:C), von Willebrand antigen (vWF:ag), von Willebrand ristocetin cofactor (vWF:Rcof), high molecular weight multimers (HMW), and ristocetin-induced platelet aggregation (RIPA) tests, it can be possible to distinguish between von Willebrand disease types 1, 2A, 2B, 2M, 2N, 3, Hemophilia A, and pseudo von Willebrand's disease.

Methods and devices described above can be useful for analyzing bleeding and/or hemostasis prior to surgery to detect "bleeder's" having prolonged bleeding times or other hemostasis impairment. The methods can also be used for detection of intra-operative and/or post operative bleeding. The described tests can additionally detect platelet derived micro-particles and can therefore be utilized in analyzing in-vivo platelet activation for predicting potential risk of arterial thrombi in an individual.

Additional applications for which the above testing methods can be particularly useful include detecting, measuring and or monitoring the effectiveness of potential hemostasis affecting agents such as medications which intentionally or unintentionally produce or enhance anticoagulation, anti-platelet effects and/or bleeding. Exemplary medications include anti-glycoprotein IIb-IIIa (REOPRO®, Eli Lilly and Company, Indianapolis, Ind.), glycoprotein IIb-IIIa inhibitors, anti-glycoprotein IB, glycoprotein IB inhibitors, clopidogrel (PLAVIX®, Elf Sanofi Corp., Paris France), ticlopidine (TICLID®, Sanofi Corp., Paris France), dypyridamole, cilostazol (PLETAL®, Otsuka Pharmaceutical Co., LTD., Tokyo Japan), and non-steroidal anti-inflammatory medications (e.g. aspirin, naprosyn, etc.). Monitoring of an individuals blood and/or effects of potential hemostasis affecting agents can comprise conducting the described tests at time intervals during a treatment or therapy period, or over any period of interest.

An additional particularly useful application of the described tests and methods is detection, measurement and or monitoring the effectiveness of medications and or potential hemostasis affecting agents administered to intentionally produce or enhance clotting. For example, the described method can monitor the effectiveness of Desmopressin administered to increase the amount of von Willebrand factor in individuals afflicted with von Willebrand disease.

The testing methods described can also be particularly useful for detecting, measuring and/or monitoring the effects of blood platelet products, such as donor platelets, stored donor platelets, artificial platelets, or platelet substitutes (e.g. CYPLEX®, Cypress Bioscience, Inc. San Diego, Calif.). This application of the invention can be utilized for platelet product quality control purposes as well as analysis after administration of platelet products to a patient (for example by transfusion).

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. An in vitro bleeding time determination device comprising:
   a housing having an internal chamber with a longitudinal axis, an inlet in fluid communication with the internal chamber disposed at a first elevation, and a single outlet in fluid communication with the internal chamber disposed at a second elevation below the first elevation, wherein the single outlet has a flowpath perpendicular to the longitudinal axis of the internal chamber that permits fluid to flow out from the chamber;

a sheet of material spanning the flowpath through the outlet, the sheet of material having a sheet thickness and having an inner region surrounded by a peripheral region, the inner region having a rectangular opening spanning the sheet thickness, the opening having a width of from about 60 microns to about 120 microns and a length of less than 500 microns, the rectangular opening being disposed such that the opening is substantially horizontal along its length when the device is in operation; and a coating over at least a portion of a first side of the sheet of material, the coating comprising collagen type I, fibrinogen, fibronectin, and von Willebrand factor, and a substantial absence of type IV collagen.

2. The device of claim 1 wherein the first side of the sheet of material is exposed to and faces the internal chamber.

3. The device of claim 2 further comprising a collection vessel wherein at least a portion of the housing is inserted into the collection vessel and wherein blood passing through the opening through the sheet of material is collected within the collection vessel.

4. The device of claim 3 wherein the housing is sealably inserted into the collection vessel.

5. The device of claim 4 wherein the housing comprises a main body and an external lip portion, the chamber being within the main body and the lip portion being in sealable contact with the collection vessel and wherein the collection vessel is vented through a vent opening through the lip portion of the housing.

6. The device of claim 2 further comprising a sensor in sensing relation relative to the internal chamber, the sensor comprising at least one of a pressure sensor and a flow rate sensor.

7. The device of claim 1 wherein the sheet of material comprises nylon.

8. The device of claim 1 wherein the sheet of material is essentially non-porous.

9. The device of claim 1 wherein the sheet of material comprises nylon membrane having pore size of about 6 microns, wherein the coating essentially fills the membrane pores to create an essentially non-porous membrane.

10. A blood coagulation analysis system comprising:

a receiving device having an internal chamber with a longitudinal axis for receiving a blood sample, having an inlet in fluid communication with the internal chamber and having a single outlet in fluid communication with the internal chamber, the inlet being disposed elevationally above the outlet during operation of the device and the single outlet having a flowpath located perpendicular to the longitudinal axis of the internal chamber that permits fluid to flow out from the chamber;

a sensor configured to detect at least one of fluid pressure and flow rate within the internal chamber;

a sheet of material configured to span the flowpath through the single outlet, the sheet of material having a rectangular opening spanning a thickness of the sheet and being aligned substantially horizontal along the length of the opening; and a controller configured to receive information from the sensor and regulate at least one of flow rate and pressure within the internal chamber, the controller being configured to provide constant pressure within the internal chamber.

11. The system of claim 10 further comprising a sample vessel in fluid communication with the internal chamber of the receiving device, wherein the pressure within the internal chamber is regulated by controlling fluid flow from the sample vessel into the internal chamber.

12. The system of claim 11 wherein the sample vessel comprises a syringe and wherein the receiving device comprises a fitting reversibly attachable to the syringe.

13. The system of claim 11 wherein the sensor is disposed between the sample vessel and the receiving device.

14. The system of claim 10 wherein the pressure is maintained at substantially constant pressure of from greater than zero mmHg to less than or equal to about 200 mmHg.

15. The system of claim 14 wherein the pressure is maintained at substantially constant pressure less than or equal to about 100 mmHg.

16. The system of claim 15 wherein the substantially constant pressure is from about 5 mmHg to about 80 mmHg.

17. The system of claim 10 wherein the sheet of material comprises nylon and a coating mixture, the coating mixture comprising type 1 collagen.

18. The system of claim 17 wherein the mixture further comprises one or more of fibrinogen, fibronectin and von Willebrand factor.

19. The system of claim 10 configured to measure a bleeding time based upon a time period between an initiation of flow of the blood sample into the chamber and a point of time where flow through the outlet substantially ceases.

20. The system of claim 19 wherein the point of time is determined based upon information from the sensor.

21. A method for analyzing blood coagulation, comprising:

providing a device comprising an internal chamber with a longitudinal axis, an inlet port in fluid communication with the internal chamber and a single outlet disposed elevationally lower than the inlet port and in fluid communication with the internal chamber wherein the single outlet has a flowpath located perpendicular to the longitudinal axis of the internal chamber that permits fluid to flow out of the chamber;

providing a source of blood in selective fluid communication with the internal chamber through the inlet port;

providing a sensor configured to sense at least one of pressure and flow rate within the internal chamber;

providing a sheet of material spanning a cross-section of the flowpath in the outlet, the sheet of material having a single opening providing fluid passage through the sheet;

initiating blood flow from the source into the device;

routing at least one of pressure information and flow rate information from the chamber through the sensor to a controller;

forming a clot blockage of the opening; and utilizing the controller to control the flow rate from the source through the inlet port during clot formation to maintain a predetermined shear force within the internal chamber.

22. The method of claim 21 wherein the source is a syringe.

23. The method of claim 21 wherein the sheet of material comprises a substance over at least a portion of a sheet surface, the substance comprising collagen type I and an absence of collagen type IV.

24. The method of claim 23 wherein the substance further comprises one or more of fibrinogen, fibronectin and von Willebrand factor.

25. The method of claim 21 wherein the flow rate within the device is maintained at a value of from about 1 ml/min to about 10 ml/min.

26. The method of claim 21 further comprising determining a first time measurement corresponding to time elapsed between the initiating blood flow and a cessation of blood flow through the opening.

27. The method of claim 26 wherein the first time measurement comprises detecting a pressure increase due to the cessation of blood flow.

28. The method of claim 26 wherein the first time measurement comprises visually detecting the cessation of blood flow.

29. The method of claim 26 wherein the blood is obtained from an individual and wherein the method is performed to analyze blood prior to surgery on the individual.

30. The method of claim 26 wherein the blood is obtained from an individual and wherein the method is performed to analyze blood during surgery on the individual.

31. The method of claim 26 wherein the blood is obtained from an individual and wherein the method is performed to analyze blood after surgery on the individual.

32. The method of claim 26 wherein the blood is obtained from an individual and further comprising:
    determining whether the first time measurement is within a predetermined range of time that is considered to be normal; and
    utilizing at least one additional technique, further analyzing blood from the individual to obtain supplemental results, the at least one additional technique being selected from the group consisting of prothrombin time, complete blood count, and partial thromboplastin time.

33. The method of claim 26 wherein the blood is a first sample of blood obtained from an individual, wherein the device is a first device, wherein the sheet of material is a first sheet of material, and further comprising:
    providing a second device comprising a second internal chamber, an inlet port in fluid communication with the internal chamber and a single outlet in fluid communication with the second internal chamber;
    providing a second sheet of material spanning a cross-section of the outlet of the second device, the sheet of material having a single opening providing fluid passage through the second sheet;
    utilizing a second sample of blood from the individual, initiating blood flow into the second device;
    forming a clot blockage of the opening through the second sheet; and
    determining a second time measurement corresponding to time elapsing between the initiating blood flow into the second device and cessation of blood flow through the opening through the second sheet.

34. The method of claim 33 wherein a first flow rate is maintained within the first device and a second flow rate is maintained within the second device, the second flow rate being different than the first flow rate.

35. The method of claim 33 wherein a first shear rate is maintained within the first device and a second shear rate is maintained in the second device, the second shear rate being higher than the first.

36. The method of claim 35 wherein the first shear rate is less than or equal to about 1000 sec$^{-1}$.

37. The method of claim 35 wherein the second shear rate is greater than or equal to about 1000 sec$^{-1}$.

38. The method of claim 37 wherein the second shear rate is greater than or equal to about 2000 sec$^{-1}$.

39. The method of claim 37 wherein the second shear rate is greater than or equal to about 8000 sec$^{-1}$.

40. The method of claim 33 wherein the first device is provided at a first time and the second device is provided at a second time, the second time being spaced from the first time by a time interval, and wherein the method is utilized to monitor bleeding time during one of medical treatment or therapy.

41. The method of claim 33 wherein the method is utilized to monitor effectiveness of at least one potential hemostasis affecting agent administered to the individual selected from the group consisting of anticoagulation medications, anti-platelet therapy medications, non-steroidal anti-inflammatory medications, Desmopressins, donor platelets, artificial platelets and platelet substitutes.

42. The method of claim 33 wherein the first sheet is at least partially coated with a first coating substance comprising type I collagen, and wherein the second sheet is at least partially coated with a second coating substance comprising collagen, the second coating substance additionally comprising one or more coagulation agent not present in the first coating substance.

43. The method of claim 42 wherein the one or more coagulation agent is selected from the group consisting of fibrinogen, von Willebrand factor, fibronectin or fibronectin fragments or peptides, prothrombin, thrombin, thrombin-receptor-activating peptide, ancrod, prekallekrein, high molecular weight kinninogen, reptilase, coagulation factor XII, activated coagulation factor XII, coagulation factor IX, activated coagulation factor IX, coagulation factor VIII, activated coagulation factor VIII, coagulation factor V, activated coagulation factor V, coagulation factor VII, activated coagulation factor VII, tissue thromboplastin, tissue factor/factor VII complex, phospholipids, integrins, antibodies, immunoglobulin superfamily molecules, adenosine diphosphate, thromboxane, arachidonic acid, ristocetin, botrocetin, and recombinant forms of any of the listed protein factors and agents.

44. The method of claim 42 further comprising comparing the first time measurement and the second time measurement.

45. The method of claim 33 further comprising adding one or more coagulation agent to the second sample prior to initiating flow into the second device, the one or more coagulation agent being selected from the group consisting of fibrinogen, von Willebrand factor, fibronectin or fibronectin fragments or peptides, prothrombin, thrombin, thrombin-receptor-activating peptide, ancrod, prekallekrein, high molecular weight kinninogen, reptilase, coagulation factor XII, activated coagulation factor XII, coagulation factor IX, activated coagulation factor IX, coagulation factor VIII, activated coagulation factor VIII, coagulation factor V, activated coagulation factor V, coagulation factor VII, activated coagulation factor VII, tissue thromboplastin, tissue factor/factor VII complex, phospholipids, integrins, antibodies, immunoglobulin superfamily molecules, adenosine diphosphate, thromboxane, arachidonic acid, ristocetin, botrocetin, and recombinant forms of any of the listed protein factors and agents.

46. The method of claim 45 further comprising comparing the first time measurement and the second time measurement.

* * * * *

UNITED STATES PATENT AND TRADEMARK OFFICE
CERTIFICATE OF CORRECTION

| | | |
|---|---|---|
| PATENT NO. | : 7,071,001 B2 | Page 1 of 1 |
| APPLICATION NO. | : 10/754776 | |
| DATED | : July 4, 2006 | |
| INVENTOR(S) | : Brubaker | |

It is certified that error appears in the above-identified patent and that said Letters Patent is hereby corrected as shown below:

On the title page
Item (56) References Cited, U.S. Patent Documents, Line 6 – Replace "3,749,046 A 07/1973 Pin" with --3,749,646 A 07/1973 Pirt--.

Item (57) Abstract, Line 3 – Replace "a portion the" with --a portion of the--.

Column 1, Line 40 – Replace "can be due the" with --can be due to the--.

Column 4, Line 45 – Replace "disposed or" with --disposed of--.

Column 4, Line 60 – Replace "inlet 12" with --inlet 22--.

Column 5, Line 25 – Replace "device 12" with --device assembly 12--.

Column 5, Line 61 – Replace "more openings" with --more vent openings--.

Column 8, Line 50 – Replace "enhance on or" with --enhance one or--.

Column 10, Line 6 – Delete "activated" and insert --activated coagulation factor VIII, coagulation factor V, activated coagulation factor V,--.

Signed and Sealed this

First Day of May, 2007

JON W. DUDAS
*Director of the United States Patent and Trademark Office*